US007034144B2

(12) United States Patent
van Dongen et al.

(10) Patent No.: US 7,034,144 B2
(45) Date of Patent: Apr. 25, 2006

(54) MOLECULAR DETECTION OF CHROMOSOME ABERRATIONS

(75) Inventors: Jacobus Johannus Maria van Dongen, Nieuwerker aan de IJssel (NL); Anthonie Willem Langerak, Barendrecht (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 9 days.

(21) Appl. No.: 10/739,870

(22) Filed: Dec. 18, 2003

(65) Prior Publication Data

US 2004/0180366 A1    Sep. 16, 2004

Related U.S. Application Data

(63) Continuation of application No. 09/439,040, filed on Nov. 12, 1999, now Pat. No. 6,730,474, which is a continuation of application No. PCT/NL98/00270, filed on May 13, 1998.

(30) Foreign Application Priority Data

May 13, 1997 (EP) .................................. 97201440

(51) Int. Cl.
C07H 21/04        (2006.01)
(52) U.S. Cl. ......................................... 536/24.3; 435/6
(58) Field of Classification Search ............... 536/23.1, 536/24.3, 24.32, 24.33; 435/6
See application file for complete search history.

(56) References Cited

U.S. PATENT DOCUMENTS

| 4,681,840 A | 7/1987 | Stephenson et al. |
|---|---|---|
| 4,707,440 A | 11/1987 | Stavrianopoulos |
| 4,755,458 A | 7/1988 | Rabbani et al. |
| 4,843,122 A | 6/1989 | Stavrianopoulos |
| 4,849,208 A | 7/1989 | Stavrianopoulos |
| 4,849,505 A | 7/1989 | Stavrianopoulos |
| 4,868,103 A | 9/1989 | Stavrianopoulos et al. |
| 4,892,817 A | 1/1990 | Pawlak |
| 4,912,034 A | 3/1990 | Kalra et al. |
| 4,943,523 A | 7/1990 | Stavrianopoulos |
| 4,952,685 A | 8/1990 | Stavrianopoulos |
| 4,968,603 A | 11/1990 | Slamon et al. |
| 4,994,373 A | 2/1991 | Stavrianopoulos et al. |
| 5,013,831 A | 5/1991 | Stavrianopoulos |
| 5,015,568 A | 5/1991 | Tsujimoto et al. |
| 5,079,147 A | 1/1992 | Showe et al. |
| 5,082,783 A | 1/1992 | Ernst et al. |
| 5,149,628 A | 9/1992 | Croce |
| 5,175,269 A | 12/1992 | Stavrianopoulos |
| 5,198,338 A | 3/1993 | Croce |
| 5,241,060 A | 8/1993 | Engelhardt et al. |
| 5,242,795 A | 9/1993 | Croco |
| 5,244,787 A | 9/1993 | Key et al. |
| 5,258,507 A | 11/1993 | Cruickshank et al. |
| 5,260,433 A | 11/1993 | Engelhardt et al. |
| 5,369,008 A | 11/1994 | Arlinghaus et al. |
| 5,439,649 A | 8/1995 | Tseung et al. |
| 5,447,841 A | 9/1995 | Gray et al. |
| 5,472,842 A | 12/1995 | Stokke et al. |
| 5,487,970 A | 1/1996 | Rowley et al. |
| 5,491,224 A | 2/1996 | Bittner et al. |
| 5,492,837 A | 2/1996 | Naser-Kolahzadeh et al. |
| 5,506,350 A | 4/1996 | Bittner et al. |
| 5,512,433 A | 4/1996 | Cruickshank et al. |
| 5,529,925 A | 6/1996 | Morris et al. |
| 5,538,846 A | 7/1996 | Meeker |
| 5,538,869 A | 7/1996 | Siciliano et al. |
| 5,547,838 A | 8/1996 | Nisson et al. |
| 5,567,586 A | 10/1996 | Croce |
| RE35,491 E | 4/1997 | Cline et al. |
| 5,622,829 A | 4/1997 | King et al. |
| 5,633,135 A | 5/1997 | Croce et al. |
| 5,633,136 A | 5/1997 | Croce et al. |
| 5,633,365 A | 5/1997 | Stokke et al. |
| 5,639,602 A | 6/1997 | Rashtchian et al. |
| 5,648,481 A | 7/1997 | Parodos et al. |
| 5,663,319 A | 9/1997 | Bittner et al. |
| 5,665,549 A | 9/1997 | Pinkel et al. |
| 5,677,130 A | 10/1997 | Meeker |
| 5,679,517 A | 10/1997 | Evans et al. |
| 5,684,142 A | 11/1997 | Mishra et al. |
| 5,693,464 A | 12/1997 | Trent et al. |
| 5,695,976 A | 12/1997 | Jørgensen et al. |
| 5,698,398 A | 12/1997 | Shassere et al. |
| 5,700,921 A | 12/1997 | Westling et al. |

(Continued)

FOREIGN PATENT DOCUMENTS

DE        19610255        9/1997

(Continued)

OTHER PUBLICATIONS

Tkachuk et al. Science, vol. 250: 559-562, Oct. 1990.*

(Continued)

*Primary Examiner*—Kenneth R. Horlick
*Assistant Examiner*—Cynthia Wilder
(74) *Attorney, Agent, or Firm*—Finnegan, Henderson, Farabow, Garrett & Dunner, LLP

(57) ABSTRACT

The invention relates to the field of cytogenetics and the application of genetic diagnostic techniques in pathology and hematology. Specifically, the invention relates to nucleic acid probes that can be used in hybridization techniques for the detection of chromosomal aberrations and other gene rearrangements such as immunoglobulin and T-cell receptor gene rearrangements. The probes provided by the invention are a distinct and balanced set of probes of comparable size, each preferably being from 1 to 100 kb, or smaller, and flanking a potential breakpoint in a chromosome.

11 Claims, No Drawings

U.S. PATENT DOCUMENTS

| | | | |
|---|---|---|---|
| 5,721,098 A | 2/1998 | Pinkel et al. | |
| 5,731,153 A | 3/1998 | Lucas et al. | |
| 5,750,400 A | 5/1998 | Murphy et al. | |
| 5,756,294 A | 5/1998 | White et al. | |
| 5,756,696 A | 5/1998 | Gray et al. | |
| 5,759,781 A | 6/1998 | Ward et al. | |
| 5,770,421 A | 6/1998 | Morris et al. | |
| 5,776,688 A | 7/1998 | Bittner et al. | |
| 5,786,181 A | 7/1998 | Stassi et al. | |
| 5,789,161 A | 8/1998 | Morrison et al. | |
| 5,801,021 A | 9/1998 | Gray et al. | |
| 5,804,384 A | 9/1998 | Müller et al. | |
| 5,808,026 A | 9/1998 | Cohen et al. | |
| 5,821,328 A | 10/1998 | King et al. | |
| 5,824,478 A | 10/1998 | Müller | |
| 5,837,466 A | 11/1998 | Lane et al. | |
| 5,846,749 A | 12/1998 | Slamon et al. | |
| 5,854,409 A | 12/1998 | Westling et al. | |
| 5,856,089 A | 1/1999 | Wang et al. | |
| 5,856,097 A | 1/1999 | Pinkel et al. | |
| 5,858,663 A | 1/1999 | Nisson et al. | |
| 5,888,734 A | 3/1999 | Cremer et al. | |
| 5,892,010 A | 4/1999 | Gray et al. | |
| 5,922,543 A | 7/1999 | Cremer | |
| 5,925,519 A | 7/1999 | Jensen et al. | |
| 5,939,265 A | 8/1999 | Cohen et al. | |
| 5,955,367 A | 9/1999 | Adams et al. | |
| 5,958,681 A | 9/1999 | Wetmur et al. | |
| 5,965,362 A | 10/1999 | Pinkel et al. | |
| 5,968,734 A | 10/1999 | Aurias et al. | |
| 5,976,790 A | 11/1999 | Pinkel et al. | |
| 5,994,071 A | 11/1999 | Ross et al. | |
| 5,994,076 A | 11/1999 | Chenchik et al. | |
| 5,998,135 A | 12/1999 | Rabbani et al. | |
| 6,005,095 A | 12/1999 | Capaccioli et al. | |
| 6,007,994 A | 12/1999 | Ward et al. | |
| 6,025,126 A * | 2/2000 | Westbrook | 435/6 |
| 6,037,129 A | 3/2000 | Cole et al. | |
| 6,040,140 A | 3/2000 | Croce et al. | |
| 6,083,709 A | 7/2000 | Reynolds et al. | |
| 6,100,029 A | 8/2000 | Lapidus et al. | |
| 6,121,419 A | 9/2000 | Rowley et al. | |
| 6,127,118 A | 10/2000 | Meeker | |
| 6,132,961 A | 10/2000 | Gray et al. | |
| 6,150,110 A | 11/2000 | Fletcher et al. | |
| 6,159,685 A | 12/2000 | Pinkel et al. | |
| 6,174,674 B1 | 1/2001 | Morris et al. | |
| 6,174,681 B1 | 1/2001 | Halling et al. | |
| 6,203,977 B1 | 3/2001 | Ward et al. | |
| 6,214,558 B1 | 4/2001 | Shuber et al. | |
| 6,218,529 B1 | 4/2001 | An et al. | |
| 6,221,607 B1 | 4/2001 | Tsipouras et al. | |
| 6,239,271 B1 | 5/2001 | Rabbani et al. | |
| 6,251,601 B1 | 6/2001 | Bao et al. | |
| 6,255,465 B1 | 7/2001 | Ferguson-Smith et al. | |
| 6,268,184 B1 | 7/2001 | Gray et al. | |
| 6,270,760 B1 | 8/2001 | Adams et al. | |
| 6,270,971 B1 | 8/2001 | Ferguson-Smith et al. | |
| 6,277,569 B1 | 8/2001 | Bittner et al. | |
| 6,280,721 B1 | 8/2001 | Adams et al. | |
| 6,280,929 B1 | 8/2001 | Gray et al. | |
| 6,284,882 B1 | 9/2001 | Wu-Wong et al. | |
| 6,335,167 B1 | 1/2002 | Pinkel et al. | |
| 6,344,315 B1 | 2/2002 | Gray et al. | |
| 6,352,829 B1 | 3/2002 | Chenchik et al. | |
| 6,358,682 B1 | 3/2002 | Jaffee et al. | |
| 6,358,685 B1 | 3/2002 | Wetmur et al. | |
| 6,368,791 B1 | 4/2002 | Felix et al. | |
| 6,376,188 B1 | 4/2002 | Halling et al. | |
| 6,391,592 B1 | 5/2002 | Su et al. | |
| 6,414,133 B1 | 7/2002 | Dietz-Band et al. | |
| 6,429,303 B1 | 8/2002 | Green et al. | |
| 6,451,529 B1 | 9/2002 | Jensen et al. | |
| 6,451,551 B1 | 9/2002 | Zhan et al. | |
| 6,451,997 B1 | 9/2002 | Morris et al. | |
| 6,475,720 B1 | 11/2002 | Gray et al. | |
| 6,489,455 B1 | 12/2002 | Chenchik et al. | |
| 6,500,612 B1 | 12/2002 | Gray et al. | |
| 6,506,563 B1 | 1/2003 | Ward et al. | |
| 6,514,693 B1 | 2/2003 | Lansdorp | |
| 6,544,784 B1 | 4/2003 | Bullerdiek et al. | |
| 6,548,259 B1 | 4/2003 | Ward et al. | |
| 6,566,058 B1 | 5/2003 | Cardy | |
| 6,566,068 B1 | 5/2003 | Rabbani et al. | |
| 6,569,626 B1 | 5/2003 | Bittner et al. | |
| 6,573,042 B1 | 6/2003 | Wang | |
| 6,573,043 B1 | 6/2003 | Cohen et al. | |
| 6,576,421 B1 | 6/2003 | Westbrook | |
| 6,607,877 B1 | 8/2003 | Gray et al. | |
| 6,610,498 B1 | 8/2003 | Berendes et al. | |
| 6,686,165 B1 | 2/2004 | van Dongen et al. | |
| 6,689,875 B1 | 2/2004 | Dierlamm et al. | |
| 6,770,477 B1 | 8/2004 | Slamon et al. | |
| 6,808,878 B1 | 10/2004 | Gray et al. | |
| 2001/0026921 A1 | 10/2001 | Rabbani et al. | |
| 2002/0009720 A1 | 1/2002 | Van De Ven et al. | |
| 2002/0019001 A1 | 2/2002 | Light | |
| 2002/0028460 A1 | 3/2002 | Pinkel et al. | |
| 2002/0042056 A1 | 4/2002 | van Dongen et al. | |
| 2002/0098510 A1 | 7/2002 | Su et al. | |
| 2002/0132246 A1 | 9/2002 | Kallioniemi et al. | |
| 2002/0138857 A1 | 9/2002 | Ghayur | |
| 2002/0160409 A1 | 10/2002 | Halling et al. | |
| 2002/0177130 A1 | 11/2002 | Gray et al. | |
| 2002/0182586 A1 | 12/2002 | Morris et al. | |
| 2002/0182628 A1 | 12/2002 | Dietz-Band et al. | |
| 2002/0182701 A1 | 12/2002 | Chang et al. | |
| 2002/0192692 A1 | 12/2002 | Palanisamy et al. | |
| 2003/0021813 A1 | 1/2003 | Chovan et al. | |
| 2003/0022178 A1 | 1/2003 | Schneewind et al. | |
| 2003/0027752 A1 | 2/2003 | Steward et al. | |
| 2003/0039658 A1 | 2/2003 | Estable et al. | |
| 2003/0039966 A1 | 2/2003 | Hering et al. | |
| 2003/0040005 A1 | 2/2003 | Jensen et al. | |
| 2003/0059790 A1 | 3/2003 | Jaffee et al. | |
| 2003/0087248 A1 | 5/2003 | Morrison et al. | |
| 2003/0087865 A1 | 5/2003 | Golub et al. | |
| 2003/0096255 A1 | 5/2003 | Felix et al. | |
| 2003/0099987 A1 | 5/2003 | Westbrook | |
| 2003/0108943 A1 | 6/2003 | Gray et al. | |
| 2003/0124563 A1 | 7/2003 | Gerdes | |
| 2003/0124629 A1 | 7/2003 | Tse et al. | |
| 2003/0129626 A1 | 7/2003 | Nielsen | |
| 2003/0143524 A1 | 7/2003 | Lerner | |
| 2003/0148270 A1 | 8/2003 | Gray et al. | |
| 2003/0148382 A1 | 8/2003 | Sun et al. | |
| 2003/0152987 A1 | 8/2003 | Cohen et al. | |
| 2003/0157527 A1 | 8/2003 | Lastrucci | |
| 2003/0176682 A1 | 9/2003 | Dlerlamm et al. | |
| 2003/0190654 A1 | 10/2003 | Heidenreich et al. | |
| 2003/0198977 A1 | 10/2003 | Nolan et al. | |
| 2003/0235840 A1 | 12/2003 | Ward et al. | |
| 2004/0009493 A1 | 1/2004 | Mohammed et al. | |
| 2004/0029142 A1 | 2/2004 | Schon | |
| 2004/0072188 A1 | 4/2004 | Ambrose et al. | |
| 2004/0096872 A1 | 5/2004 | Gray et al. | |
| 2004/0110227 A1 | 6/2004 | Levanon et al. | |
| 2004/0180349 A1 | 9/2004 | Kaye et al. | |
| 2004/0235039 A1 | 11/2004 | Gray et al. | |
| 2005/0118634 A1 | 6/2005 | Pinkel et al. | |
| 2005/0137389 A1 | 6/2005 | Gray et al. | |

FOREIGN PATENT DOCUMENTS

| | | |
|---|---|---|
| EP | 0 181 635 | 5/1986 |
| EP | 0 430 402 A2 | 6/1991 |
| EP | 0 500 290 A2 | 8/1992 |
| EP | 0 727 487 | 8/1996 |
| EP | 0 549 709 B1 | 1/1997 |
| EP | 0 825 198 | 2/1998 |
| EP | 0 878 552 | 11/1998 |
| EP | 0 885 971 A2 | 12/1998 |
| EP | 0 430 402 B1 | 1/1999 |
| EP | 0 558 732 B1 | 3/1999 |
| EP | 0 631 635 B1 | 9/2001 |
| EP | 1 134 293 A2 | 9/2001 |
| EP | 1 146 892 B1 | 8/2003 |
| EP | 1 365 033 A1 | 11/2003 |
| EP | 1 369 482 A1 | 12/2003 |
| EP | 0 787 805 A3 | 1/2004 |
| EP | 1 388 589 A1 | 2/2004 |
| EP | 1 314 980 A3 | 3/2004 |
| EP | 1 394 715 A1 | 3/2004 |
| EP | 1 362 929 A3 | 5/2004 |
| EP | 1 415 659 A2 | 5/2004 |
| EP | 1 422 524 A1 | 5/2004 |
| WO | WO 89/11101 | 11/1989 |
| WO | WO 90/05789 | 5/1990 |
| WO | WO 91/07489 | 5/1991 |
| WO | WO 91/09129 | 6/1991 |
| WO | WO 91/13172 | 9/1991 |
| WO | WO 92/00311 | 1/1992 |
| WO | WO 92/16662 | 10/1992 |
| WO | WO 93/03187 | 2/1993 |
| WO | WO 93/06245 | 4/1993 |
| WO | WO 93/11265 | 6/1993 |
| WO | WO 93/17128 | 9/1993 |
| WO | WO 93/24653 | 12/1993 |
| WO | WO 94/06812 | 3/1994 |
| WO | WO 94/06936 | 3/1994 |
| WO | WO 94/09022 | 4/1994 |
| WO | WO 94/24308 | 10/1994 |
| WO | WO 95/13398 | 5/1995 |
| WO | WO 95/17430 | 6/1995 |
| WO | WO 95/31545 | 11/1995 |
| WO | WO 96/00234 | 1/1996 |
| WO | WO 96/17958 | 6/1996 |
| WO | WO 96/18906 | 6/1996 |
| WO | WO 97/18325 | 5/1997 |
| WO | WO 98/37231 | 8/1998 |
| WO | WO 98/49275 | 11/1998 |
| WO | WO 98/51817 | 11/1998 |
| WO | WO 99/00520 | 1/1999 |
| WO | WO 99/51961 | 10/1999 |
| WO | WO 99/63342 | 12/1999 |
| WO | WO 00/06773 | 2/2000 |
| WO | WO 00/24940 | 5/2000 |
| WO | WO 00/32810 | 6/2000 |
| WO | WO 00/60119 | 10/2000 |
| WO | WO 01/06001 | 1/2001 |
| WO | WO 01/20027 | 3/2001 |
| WO | WO 01/20033 | 3/2001 |
| WO | WO 01/23621 | 4/2001 |
| WO | WO 01/29265 | 4/2001 |
| WO | WO 01/40301 | 6/2001 |
| WO | WO 01/66776 | 9/2001 |
| WO | WO 01/75160 | 10/2001 |
| WO | WO 01/88500 | 11/2001 |
| WO | WO 02/18601 | 3/2002 |
| WO | WO 02/28900 | 4/2002 |
| WO | WO 02/44411 | 6/2002 |
| WO | WO 03/33668 | 4/2003 |
| WO | WO 03/39438 | 5/2003 |
| WO | WO 03/40366 | 5/2003 |
| WO | WO 03/54207 | 7/2003 |
| WO | WO 03/66898 | 8/2003 |

OTHER PUBLICATIONS du Manoir et al., "Detection of complete and partial chromosome gains and losses by comparative genomic in situ hybridization", Human Genetics, 90:590-610; 1993.

Thompson et al., Cytogenetic Profiling Using Fluorescence In Situ Hybridization (FISH) and Comparative Genomic Hybridization (CGH), Journal of Cellular Biochemistry, 17G:139-143 (1993).

Tkachuk et al., "Clinical Applications of Fluorescence in situ Hybridization", Genetics Analysis Techniques and Applications, 8(2):67-74, 1991.

Tkachuk et al., "Detection of bcr-abl Fusion in Chronic Myelogeneous Leukemia by in Situ Hybridization", Science, Oct. 26, 1990, pp. 559-562, vol. 250.

Nagasaki et al., "An enzyme immunoassay for carcinoembryonic antigen (CEA) with homogeneous reactivity to different CEA preparations and low cross-reactivity with CEA-related normal antigens", Journal of Immunological Methods, 1993, pp. 234-245, vol. 162, No. 2.

Lichter et al., "Rapid Detection of Human Chromosome 21 Aberrations by In Situ Hybridization," Proc. Natl. Acad. Sci. USA, vol. 85, pp. 9664-9668, Dec., 1988.

Cremer et al., "Rapid Interphase and Metaphase Assessment of Specific Chromosomal Changes in Neuroectodermal Tumor Cells by In Situ Hybridization with Chemically Modified DNA Probes," Exp. Cell Res., vol. 176, pp. 199-220, 1988.

Trask et al., "Fluorescence In Situ Hybridization to Interphase Cell Nuclei in Suspension Allows Flow Cytometric Analysis of Chromosome Content and Microscopic Analysis of Nuclear Organization," Hum. Genet, vol. 78, pp. 251-259, Mar., 1988.

Smith et al., "Studies of Nucleic Acid Reassociation Kinetics: Reactivity of Single-Stranded Tails in DNA-RNA Renaturation," Proc. Natl. Acad. Sci. USA, vol. 72, pp. 4805-4809, Dec., 1975.

Lucas et al., "Rapid Human Chromosome Aberration Analysis Using Fluorescence In Situ Hybridization," Int. J. Radiat. Biol., vol. 56, pp. 35-44, Jul., 1989.

Lichter et al., "Is Non-Isotopic In Situ Hybridization Finally Coming of Age?," Nature, vol. 345, pp. 93-94, May 3, 1990.

Emmerich et al., Interphase Cytogenetics in Paraffin Embedded Sections from Human Testicular Gem Cell Tumor Xenografts and in Corresponding Cultured Cells, Lab. Invest., vol. 61, pp. 235-242, Aug., 1989.

Manuelidis et al., "Reproducible compartmentalization of Individual Chromosome Domains in Human CNS Cell Revealed by In Situ Hybridization and Three-Dimensional Reconstruction," Chromosoma, vol. 96, pp. 397-410, 1988.

Schardin et al., "Specific Staining of Human Chromosomes in Chinese Hamster x Man Hybrid Cell Lines Demonstrates Interphase Chromosome Territories," Hum. Genet., vol. 71, pp. 281-287, 1985.

Dauwerse et al., "Rapid Detection of Chromosome 16 Inversion in Acute Nonlymphocytic Leukemia, Subtype M4: Regional Localization of the Breakpoint in 16p," Cytogenet. Cell Genet., vol. 53, pp. 126-128, 1990.

Laforgia et al., "Detailed Genetic and Physical Map of the 3p Chromosome Region Surrounding the Familial Renal Cell Carcinoma Chromosome Translocation, t(3;8)(p14.2; q24.1)," Cancer Res., vol. 53, pp. 3118-3124, 1993.

Weber-Matthiesen et al., "Translocation t(2;5) is Not a Primary Event in Hodgkin's Disease," Am. J. Pathol., vol. 149, pp. 463-467, Aug., 1996.

Pinkel et al., "Cytogenetic Analysis by In Situ Hybridization with Fluorescently Labeled Nucleic Acid Probes," Cold Spring Harb. Symp. Quant. Biol., vol. 51, pp. 151-157, 1986.

Weber-Matthiesen et al., "Rapid Immunophenotypic Characterization of Chromosomally Aberrant Cells by the New FICTION Method," Cytogenet. Cell Genet., vol. 63, pp. 123-125, 1993.

Weber-Matthiesen et al., "Simultaneous Fluorescence Immunophenotyping and Interphase Cytogenetics: A Contribution to the Characterization of Tumor Cells," J. Histochem. Cytochem., vol. 40, pp. 171-175, 1992.

Nederlof et al., "Detection of Chromosome Aberrations in interphase Tumor Nuclei by Nonradioactive In Situ Hybridization," Cancer Genet. Cytogenet., vol. 42, pp. 87-89, 1989.

Hopman et al., "Bi-color Detection of Two Target DNAs by Non-Radioactive In Situ Hybridzation," Histochemistry, vol. 85, pp. 1-4, 1986.

Van Der Plas et al., "Cytogenetic and Molecular Analysis in Philadelphia Negative CML," Blood, vol. 73, pp. 1038-1044, Mar., 1989.

Rappold et al., "Sex Chromosome Positions in Human Interphase Nuclei as Studied by In Situ Hybridization with Chromosome Specific DNA Probes," Hum. Genet., vol. 67, pp. 317-325, 1984.

Cremer et al., "Detection of Chromosome Aberrations in the Human Interphase Nucleus by Visualization of Specific Target DNAs with Radioactive and Non-Radioactive In Situ Hybridization Techniques: Diagnosis of Trisomy 18 with Probe L1.84," Hum. Genet. vol. 74, pp. 346-352, 1986.

Landegent et al., "Use of Whole Cosmid Cloned Genomic Sequences for Chromosomal Localization by Non-Radioactive In Situ Hybridization," Hum. Genet., vol. 77, pp. 366-370, 1987.

Lichter et al., "Delineation of Individual Human Chromosomes in Metaphase and Interphase Cells by In Situ Suppression Hybridization Using Recombinant DNA Libraries," Hum. Genet., vol. 80, pp. 224-234, 1988.

Nederlof et al., "Three-Color Fluorescence In Situ Hybridization for the Simultaneous Detection of Multiple Nucleic Acid Sequences," Cytometry, vol. 10, pp. 20-27, 1989.

Cremer et al., "Detection of Chromosome Aberrations in Metaphase and Interphase Tumor Cells by In Situ Hybridization Using Chromosome-Specific Library Probes," Hum. Genet., vol. 80 pp. 235-246, 1988.

Landegent et al., "Chromosomal Localization of a Unique Gene by Non-Autoradiographic In Situ Hybridization," Nature, vol. 317, pp. 175-177, 1985.

Pinkel et al., "Fluorescene in situ Hybridization with Human Chromosome-Specific Libraries: Detection of Trisomy 21 and Translocations of Chromosome 4," Proc. Natl. Acad. Sci. USA, vol. 85, pp. 9138-9142, Dec., 1988.

Pinkel et al., "Cytogenetic Analysis Using Quantitative, High-Sensitivity, Fluorescene Hybridization," Proc. Natl. Acad. Sci. USA, vol. 83, pp. 2934-2938, May, 1986.

Hopman et al., "A New Hybridocytochemical Method Based on Mercurated Nucleic Acid Probes and Sulfhydry-Hapten Ligands. I. Stability of the Mercury-Sulfhydryl Bond and Influence of the Ligand Structure on Immunochemical Detection of the Hapten," Histochemistry, vol. 84, pp. 169-178, 1986.

Egholm et al., "PNA Hybridizes to Complementary Oligonucleotides Obeying the Watson-Crick Hydrogen-Bonding Rules," Nature, vol. 365, pp. 566-568, 1993.

Kosynkina et al., "A Convenient Synthesis of Chiral Peptide Nucleic Acid (PNA) Monomers," Tetrahedron Letters, vol. 35, pp. 5173-5176, 1994.

Roberts et al., "Synthesis of Oligonucleotides Bearing the Non-Standard Bases iso-C and iso-G. Comparison of iso-C-iso-G, C-G and U-A Base-Pair Stabilities in RNA/DNA Duplexes," Tetrahedron Letters, vol. 36, pp. 3601-3604, 1995.

Mar. 1, 2005, Non-Final Office Action Issued to U.S. Appl. No. 10/229,110.

* cited by examiner

MOLECULAR DETECTION OF CHROMOSOME ABERRATIONS

CROSS-REFERENCE TO RELATED APPLICATIONS

This application is a continuation of co-pending application Ser. No.09/439,040, filed Nov. 12, 1999, now U.S. Pat. No. 6,730,474, which is a continuation of pending International Application No. PCT/NL98/00270, filed on 13 May 1998, designating the United States of America, the contents of which are incorporated by this reference.

TECHNICAL FIELD

The invention relates generally to biotechnology, and more particularly to the field of cytogenetics and the application of genetic diagnostic techniques in pathology and hematology. Specifically, the invention relates to nucleic acid probes that can be used in hybridization techniques for the detection of chromosomal aberrations and other gene rearrangements such as immunoglobulin (Ig) and T-cell receptor (TCR) gene rearrangements.

BACKGROUND

Chromosomal aberrations are a leading cause of genetic disorders or diseases, including congenital disorders and acquired diseases such as malignancies. At the base of these malignancies is the fact that all cells of a malignancy have a common clonal origin. Chromosomal aberrations in malignancies stem from rearrangements, translocations, inversions, insertions, deletions and other mutations of chromosomes, but also losses or gains of whole chromosomes are found in malignancies. In many chromosome aberrations, two different chromosomes are involved. In this way, genes (or fragments of genes) are removed from the normal physiological context of a particular chromosome and are located to a recipient chromosome, adjacent to non-related genes or fragments of genes (often oncogenes or proto-oncogenes). Such an aberrant genetic combination can be the foundation of a malignancy.

Often, such rearrangements involving two non-aberrant chromosomes happen in a somewhat established pattern. Breaks occur in either of the two chromosomes at a potential breakpoint or breakpoint cluster region, resulting in the removal of a gene or gene fragment from one chromosome and subsequent translocation of the gene or gene fragment to the other chromosome, thereby forming a rearranged chromosome where the rearranged fragments are fused in a fusion region.

Detection of chromosome aberrations can be achieved using a wide array of techniques, various of which entail modern biomolecular technology. Traditional techniques such as cytogenetic analyses by conventional chromosome banding techniques are, although highly precise, very labor intensive, require skilled personal and are expensive. Automated karyotyping is useful for some diagnostic applications, such as prenatal diagnosis, but is ineffective in analyzing the complex chromosomal aberrations of many malignancies. Furthermore, the above techniques require fresh (cultured) cells, which are not always available.

Other, more modern, techniques are Southern blotting or other nucleic acid hybridization techniques or amplification techniques such as polymerase chain reaction ("PCR") for the detection of well-defined chromosome aberrations for which suitable nucleic acid probes or primers are available. With these techniques, fresh or frozen cells and sometimes even samples after formalin fixation can be used, as long as the nucleic acid sequences to be hybridized or amplified remain intact and accessible. However, even with this modern technology, several disadvantages can be found that hamper the application of these diagnostic techniques in the rapid screening for chromosomal aberrations related to such malignancies can be found.

Southern blotting lasts 3 to 4 weeks, which is too slow for efficient diagnosis and choice of therapy in malignancies, and allows only 10–15 kb of nucleic acid sequences to be analyzed per probe analysis.

PCR, although, in essence, well-suited for rapid and massive diagnostic testing or even screening, allows only 0.1 to 2 kb of nucleic acid to be analyzed per PCR analysis, which greatly hampers rapid screening of vast stretches of chromosomes and breakpoint cluster regions within the chromosomes. An additional disadvantage of PCR is its inherent sensibility to mismatched primers. Small, normal, and physiological alterations which can always be present in the nucleic acid sequence of the gene fragment complementary to the primer hamper the reliable application of PCR and eventually give rise to false-negative results, which renders a PCR-based diagnostic test, albeit very specific, not sensitive enough for reliable diagnosis. Only a reliable diagnosis of malignancies can contribute to an understanding of the prognosis and the design of an adequate therapy.

Fluorescent in situ hybridization ("FISH") techniques are less dependent on the complete matching of nucleic acid sequences to provide positive diagnostic results. In general, FISH employs probe analyses with large, mainly unspecified, nucleic acid probes that hybridized, however, often with varying stringency, with the genes or gene fragments located at both sides of the fusion region in the rearranged chromosome in the malignant cell. Using large probes renders the FISH technique very sensitive. The binding of the co-localizing probes is generally detected either directly or indirectly with fluorochromes and visualized via fluorescence microscopy of a population of cells obtained from the sample to be tested.

However, even the currently used FISH protocols have inherent disadvantages. These disadvantages mainly relate to the selection of nucleic acid probes employed in the current FISH protocols, which can give false-positive results in the diagnosis of chromosomal aberrations. For example, probes directed against different chromosomes with a juxtaposition of signals in the case of translocation create a rather large risk of false-positive results. Hence, the diagnostic tests, although sensitive, are not specific enough to employ standard FISH techniques in massive or rapid diagnostic testing, let alone in automated testing or screening.

Thus far, generally large probes derived from cosmic clones, YAC clones, or other cloned DNA fragments, have been used as probes in FISH. The exact position of these probes in relation to the fusion region in the rearranged chromosome is unknown and these probes are of largely unspecified and varying genomic length (genomic length or distance as expressed as the number of nucleotides or bases (b)) and go, without specific selection or modification of these probes, beyond the mere labeling of the probes with the necessary reporter molecules, i.e., fluorochromes. For designing or selecting probes, little or no guidance is given in the art beyond mere suggestions as to where to localize a putative probe. False-positive results obtained with these probes may stem from a specific hybridization with a wide array of (major) repetitive sequences present throughout various chromosomes, or from cross-hybridization to homologous sequences in the genome, or from overlap of the probes used with the breakpoint cluster region or from the difference in signal intensities as far as originating from size differences of the probes. These causes of false-positive results are frequently not recognized. False-positive results are especially detrimental to rapid diagnosis if rapid or routine screening of patients is needed to detect malignancies or in evaluating treatment protocols. A false-positive result then necessitates cumbersome retesting of patients, or even unsuspecting clients that have been submitted to routine screening protocols, and can greatly alarm these people. Furthermore, translocations are generally detected with two different probes, one for each of the involved chromosomes, which probes then colocalize during the in situ hybridization in the case of a translocation, but show separate signals when no translocation is present (see, e.g., European patent applications EP 0430402 and EP 0500290; Tkachuk et al., *Science* 250:559–562 (1990); Tkachuk et al., "Clinical applications of fluorescence in situ hybridization," *Genetic analysis techniques and applications* 8:67–74 (1991). However, in practice, 2 to 4% of normal interphase cells tested by FISH will show false-positive results due to the fact that the two probes colocalize by chance. An additional disadvantage of the current FISH protocols is that it is, in practice, necessary to know both chromosomes that are involved in the translocation as well as the relevant breakpoint regions of both chromosomes to define the nucleic acid probes enabling the detection of the specified translocation, while as yet unknown or ill-defined translocations originating from a well-known gene and an unknown partner gene remain undetected.

BRIEF SUMMARY OF THE INVENTION

The present invention provides nucleic acid probes that can be used in diagnostic testing for chromosome aberrations which combine a high sensitivity and a high specificity. The probes provided by the invention can hybridize in situ, in vivo or in vitro with complementary nucleic acid molecules such as (m)RNA or DNA, as, for example, transcribed by or found in (non-aberrant and/or rearranged) chromosomes.

The present invention provides for each translocation analysis a distinct and balanced pair of nucleic acid probes. The probes are distinct in that they each hybridize to a different sequence specifically selected and flanking a distinct potential breakpoint in a non-aberrant chromosome. Furthermore, the pair formed by, for example, probe A and probe B is distinct from the pair formed by, for example, probe A and probe X. Furthermore, in the above example, probes A, B and X constitute three pairs, A-B, B-X and A-X. The probes in the pair are comparable or balanced in that they are designed to be of, for example, comparable size or genomic length, with the final aim directed to facilitating the generation of signals of comparable intensity. In addition, the probes can be comparably labeled with reporter molecules, resulting in signals of comparable intensity. Also, the probes can each be labeled with a different fluorochrome, facilitating detection on one spot of different color when they colocalize when no aberration is detected. Also, the probes can be selected to react with a chromosome at respective complementary hybridization sites that are located at comparable distances at each side of a breakpoint or breakpoint cluster region of a chromosome. The distinct and balanced pair of nucleic acid probes provided by the invention entails probes that are, for example, of comparable size or genomic length, each probe of the pair, for example, being from 1 to 10 kb, or 7 to 15 kb, or 10 to 20 kb, or 15 to 30 kb, or 20 to 40 kb, or 30 to 50 kb, or 40 to 60 kb, or 50 to 70 kb, or 60 to 80 kb, or 70 to 90 kb, or 80 to 100 kb in length. By using such a distinct and balanced pair of probes flanking a breakpoint region and not overlapping the corresponding fusion region, false-positive diagnosis in hybridization studies is avoided. The invention further provides a distinct and balanced pair of nucleic acid probes, each being labeled with at least one different reporter molecule. Nucleic acid probes can be labeled with chromophores or fluorochromes (e.g., FITC or TRITC) or by introducing a hapten such as biotin or digoxigenin. Fluorochrome-labeled probes can be detected directly. Hybridization with haptenized nucleic acid probes is followed by indirect detection using chromophores, fluorochromes or enzymes such as peroxidase.

The invention further provides a distinct and balanced pair of nucleic acid probes characterized in that both probes hybridize to a single corresponding nucleic acid molecule or its complementary strand, or hybridize to one (non-aberrant) chromosome, or hybridize to a fragment thereof, possibly comprising the aberration, instead of two probes that hybridize separately to the two chromosomes that are involved in a given translocation, as currently used in hematology and oncology in general (see, e.g., Tkachuk et al., *Science* 250:559–562, (1990); Tkachuk et al., "Clinical applications of fluorescence in situ hybridization", *Genetic analysis techniques and applications*, vol. 8, 67–74, (1991)).

The invention further provides a distinct and balanced pair of nucleic acid probes which hybridize to the nucleic acid molecule at a genomic distance of no more than 100 kb, but preferably no more than 50 kb. In addition, the invention provides a distinct and balanced pair of nucleic acid probes that hybridize in situ and can, i.e., be used in diagnostic tests entailing FISH techniques. Furthermore, the invention provides a distinct and balanced pair of nucleic acid probes, which probes each hybridize in situ under varying but generally low stringent conditions to only a few DNA molecules per cell. The nucleic acid probes composed of several DNA fragments are tested either on metaphase spreads or with Southern blotting for hybridization sensitivity and specificity to select the probe to contain as little major repetitive sequences as possible to avoid high background staining. The nucleic acid probes are tested in fiber FISH (i.e., hybridization on extended single DNA fibers immobilized on glass slides), prior to being employed in diagnostic testing, for mapping and checking their relative positions.

The probes are tested, for example, to avoid using probes hybridizing two repetitive sequences. Probes can consist of sets of various oligonucleotides, thereby avoiding repetitive sequences present in a flanking region. Such sets are distinctly labeled, with separate or distinct reporter molecules for each probe (or set of oligonucleotides) that is aimed at the respective flanking region. Such probes can each consist of multiple labeled oligonucleotides, each hybridizing to a distinct area in a flanking region. One probe can, for example, contain from 10 up to 200 of such oligonucleotides, preferably from 50–150, each oligonucleotide, for example, being 10–20 nucleotides long. For example, the intron-exon structure of the MLL gene is described in the *Br. J. Haematol.*, 93:966–972 (1996). The manuscript also shows that most breakpoints in the MLL gene are located between exon 9 and exon 14. PNA-containing probes can be designed in exons 3 to 8 for the "upstream FISH probe" and in exons 15 to 31 for the "downstream FISH probe." Particularly exon 4 and exon 28 are important for probe design, because these two exons are rather large and, therefore, can contain most of the PNA probes. PNA oligonucleotides can be synthesized, for example, for their capacity to hybridize with exon 4 or exon 28 from the 119Q3 target gene and used in one cocktail as a probe for one flanking region.

The invention further provides the use of the distinct and balanced pair of probes in diagnostic testing for chromosomal aberrations. The pair of probes according to the invention can be used in the detection of nucleic acid comprising the aberration or fragments of the aberration, or in the detection of cells, in situ or in vitro, comprising the chromosome aberration. The invention thus provides a pair or pairs of distinct and balanced probes that can be used in the detection of disorders or diseases related to chromosomal aberrations, i.e., malignancies, such as hematopoietic malignancies, as further explained below. Furthermore, the invention provides a diagnostic kit or assay comprising a pair of nucleic acid probes according to the invention that can be used in the detection of disorders or diseases related to chromosomal aberrations, i.e., malignancies, such as hematopoietic malignancies. With such a diagnostic kit or assay provided by the invention, it is, for example, possible to monitor the effects of therapy and detect minimal residual disease or detect early relapse of cancer. One can also identify the origin of bone marrow cells following bone marrow transplantation. One can also detect viral sequences, and their localization in the chromosome, in cells. The present invention is described more in detail while referring to molecular detection of chromosome aberrations in hematopoietic malignancies but is widely applicable for analysis of chromosome aberrations in general.

The development of reliable probes for detection of well-defined or even ill-defined chromosome aberrations in hematological malignancies is described as a nonlimiting example to illustrate the invention. Such probes can be used for diagnosis and for molecular classification of the involved malignancies. The new probes can be used in diagnostic testing in several types of hematological malignancies with increased sensitivity, specificity, and efficacy of analysis.

DETAILED DESCRIPTION OF THE INVENTION

Each year, worldwide, many cases of hematopoietic malignancies are being diagnosed. In the European Union (~375 million inhabitants) this concerns ~98,000 patients per year. The estimated number of patients in the USA (~250 million inhabitants) is ~65,500 per year. The majority of hematological malignancies are of lymphoid origin: acute lymphoblastic leukemias ("ALL"), chronic lymphocytic leukemias, most malignant lymphomas, and multiple myelomas. The nonHodgkin's lymphomas ("NHL") form the largest group, representing approximately half of all hematopoietic malignancies. Furthermore, European epidemiological studies show that the incidence of NHL is gradually increasing (~5% per year), which indicates that NHL poses a significant public health problem in Europe and most probably throughout the Western world. Although the annual number of patients diagnosed with ALL is smaller than for NHL, ALL has a high prevalence in children, representing the most frequent malignancy in childhood.

Lymphoid malignancies consist of a broad range of ~25 different disease entities, which differ in clinical presentation, prognosis, and treatment protocols. These disease entities have been defined in the recent Revised European American Lymphoid neoplasm ("REAL") classification. In this classification, the lymphoid malignancies are divided into B-cell malignancies (~90%) and T-cell malignancies (~10%).

The diagnosis and classification of lymphoid malignancies is generally based on cytomorphology and histomorphology, complemented with immunophenotypic information via flow cytometry and/or immunohistochemistry. This immunophenotypic information appears to be valuable for classification of lymphoid malignancies, such as the classification of ALL into pro-B-ALL, common-ALL, pre-B-ALL, and several types of T-ALL. In mature B-cell malignancies with immunoglobulin (Ig) expression, the diagnosis can be supported by immunophenotypic clonality assessment via detection of single Ig light chain expression, i.e., the distribution of Igκ and Igλ positive B-cells, which is heavily skewed in the case of a B-cell malignancy.

The value of clonality assessment is based on the fact that all cells of a malignancy have a common clonal origin. In lymphoid malignancies, this is reflected by the presence of identically (clonally) rearranged Ig and T-cell receptor ("TCR") genes: clonal Ig and/or TCR gene rearrangements are found in most (90–95%) immature lymphoid malignancies and virtually all (>98%) mature lymphoid malignancies. Therefore, molecular clonality analysis of Ig and TCR genes is highly suitable for discrimination between monoclonal (malignant) and polyclonal (reactive) lymphoproliferations. Suspect lymphoproliferations should, therefore, be subjected to molecular clonality assessment.

During the last decade, the knowledge about genetic aberrations in hematopoietic malignancies has considerably increased, especially in acute leukemias and NHL. Currently, well-established chromosome aberrations are found in 35–40% of ALL and in 30–40% of NHL. These chromosome aberrations can be used as alternative or additional markers for molecular clonality assessment. More importantly, these chromosome aberrations appear to be relevant classification markers, which supplement the currently used morphological and immunophenotypic classification systems. It has been clearly demonstrated that several genetic aberrations are associated with a favorable prognosis, whereas others are associated with poor prognosis, such as t(4;11) in pro-B-ALL and t(9;22) in common-ALL. Several treatment protocols have started to use this information for stratification of treatment. Therefore, it can be anticipated that rapid and reliable detection of well-defined genetic aberrations will become essential in the diagnosis and management of hematopoietic malignancies.

Several different types of chromosome aberrations have been identified in ALL and NHL. The chromosome aberrations in precursor-B-ALL mainly concern translocations, which result in fusion genes, encoding for fusion proteins with new or modified functions. Examples include the E2A-PBX and BCR-ABL fusion proteins, resulting from t(1;19) and t(9;22), respectively. Another important chromosome region, the 11q23 region with the MLL gene, is involved in several types of translocations in acute leukemias. In these 11q23 translocations, different partner genes are involved, leading to different fusion proteins. One of them is t(4;11), which is observed in ~70% of infant acute leukemias. Many chromosome aberrations in T-ALL and NHL involve Ig or TCR gene sequences in combination with oncogene sequences. These chromosome aberrations do not give rise to fusion proteins, but result in increased or stabilized expression of the involved oncogene, thereby contributing to uncontrolled growth. They occur at relatively high frequency in particular disease categories, such as t(14;18), with involvement of the BCL2 gene in ~90% of follicular lymphomas and t(11;14) with involvement of the BCL1/Cyclin D1 gene in ~70% of mantle cell lymphomas.

From origin, cytogenetic analysis of chromosomes has been the standard technique for detection of chromosome aberrations. This technique needs the presence of cells in metaphase, which generally requires various cell culture systems, depending on the type of malignancy. The success rate for obtaining reliable karyograms is highly dependent on the type of malignancy and the experience of the laboratory and ranges from less than 50% to over 90%. Furthermore, some chromosome aberrations cannot or can hardly be detected by cytogenetic analysis such as TAL1 deletions in T-ALL and t(12;21) in precursor-B-ALL. Therefore, in the case of well-established chromosome aberrations, the labor-intensive and time-consuming classical cytogenetics is now being replaced by molecular techniques. The molecular analysis of genetic aberrations can be performed with Southern blotting, polymerase chain reaction (PCR) techniques, and FISH techniques.

Southern blot analysis has long been the most reliable molecular method for detection of well-established chromosome aberrations, but this technique is dependent on the availability of suitable DNA probes, which recognize all relevant breakpoint cluster regions of the involved chromosome aberrations. The latter probably explains why BCL2 and BCL1/Cyclin D1 gene aberrations are detectable by Southern blotting in only 75% of follicular lymphomas and in only 50% of mantle cell lymphomas, respectively. Furthermore, Southern blot analysis is time-consuming and requires relatively large amounts of high-quality DNA derived from fresh or frozen cell samples.

Over the last five years, PCR-based techniques have been developed as alternatives for Southern blotting. PCR techniques have the advantage that they are rapid and require minimal amounts of medium-quality DNA, which might even be obtained from formalin-fixed paraffin-embedded tissue samples. Also, mRNA can be used after reverse transcription (RT) into cDNA. RT-PCR is especially valuable in the case of chromosome aberrations with fusion genes and fusion transcripts, such as is frequently seen in precursor-B-ALL and in t(2;5) in anaplastic large cell lymphoma. Despite these obvious advantages, the broad application of PCR techniques for detection of chromosome aberrations in hematopoietic malignancies is hampered by several problems. False-negative PCR results can be obtained if the DNA or mRNA from formalin fixed paraffin-embedded tissue samples is less optimal than anticipated, or when primers are mismatching. False-positive results might be obtained due to cross-contamination of PCR products between samples from different patients; especially in the case of RT-PCR studies of fusion gene transcripts, it might be difficult to exclude false-positive results. Finally, routine PCR analysis can only be used to study relatively small fusion regions of chromosome breakpoints (<2 kb). This implies that multiple oligonucleotide primer sets are needed to cover the most important breakpoint and fusion regions, whereas it will be difficult to study large breakpoint or fusion regions (>10 kb). This explains the lower detectability of chromosome aberrations and, thus, again the presence of false-negative results at the DNA level by PCR as compared to Southern blotting.

A major advantage of FISH techniques as compared to cytogenetic analysis, Southern blotting, and PCR analysis is that FISH can be performed on the interphase nuclei of all kinds of tissue and cell samples and that no need for extraction of DNA or mRNA exists. In FISH techniques generally, large DNA probes (>25 kb) are used, which are located around the breakpoint regions of the two chromosomes of the studied chromosome aberration. This implies that FISH probes can scan much larger regions than Southern blot probes or PCR primers. This advantage is especially important for detection of breakpoints outside the traditional breakpoint cluster regions. Furthermore, the use of large fluorescently labeled DNA probes allows direct and rapid visualization of deletions and translocations of the studied gene regions. Application of the latest generation of fluorescent microscopes with multiple fluorochrome filter combinations, CCD camera, and appropriate computer software allows the combined use of multiple FISH probes, which are labeled with different fluorochromes.

The availability of suitable probes is the main limiting factor in using FISH technology for detection of chromosome aberrations. Thus far, generally cosmid clones, YAC clones, or other cloned DNA fragments have been used without specific selection or modification of these probes. For many of these probes, the position in the genome is not precisely known; they often even overlap with breakpoint cluster regions, and they often contain repetitive sequences which cause high background staining. Furthermore, translocations are generally detected by use of two different probes, one for each of the involved chromosomes; these two probes are assumed to colocalize in case of a translocation, but show separate signals if no translocation is present. However, in practice, 2 to 4% of normal interphase cells will show false-positive results due to the fact that the two signals colocalize by chance.

For routine applicability of FISH techniques or other probe analysis assays or kits for the detection of chromosome aberrations in the diagnosis and classification of hematopoietic malignancies, it is necessary to design distinct and balanced probes.

The probes of the invention are selected to form a distinct and balanced pair of nucleic acid probes; size of the probes is each within certain limits of the genomes to be detected (e.g., 1–10, or 10–30, or 20–40, or 30–50, or 40–60 kb), with the final aim being that the intensity of the fluorescent signals of the various probes is comparable.

In an additional embodiment of the invention, the position of the probes constituting the pair is determined precisely, i.e., no overlap with breakpoint cluster regions, the relevant breakpoints are preferably located within 50 kb or preferably even within 25 kb of either probe, and an additional probe pair has to be designed if two breakpoint regions of a particular chromosome aberration are separated for more than 30–50 kb, depending on the exact position of the probes.

In a further embodiment, the nucleic acid probes do not contain (major) repetitive sequences and do not cross-hybridize, which results in high background staining. For this reason, the nucleic acid probes composed of several fragments can be tested either on metaphase spreads or with Southern blotting for hybridization sensitivity and specificity.

The nucleic acid probes can, alternatively or additionally, be tested in fiber FISH prior to being employed in diagnostic testing for mapping and checking their relative positions.

It has additionally been found that detection of chromosome breakpoints becomes easier and more reliable if two separate probes, labeled with two different fluorochromes, constituting the pair are designed around one of the breakpoint regions of a chromosome aberration. This will lead to colocalization of the signals if no breakpoint is present.

However if a breakpoint occurs in the studied breakpoint region, the two differently labeled probes will result in two separate signals.

In addition, the design of a third probe (labeled with a third fluorochrome) and, thus, the design of two additional distinct pairs of probes for the partner gene of the chromosome aberration allow precise identification of the chromosome aberration.

Chromosome aberrations found in malignancies are useful for molecular classification, such as in the case of acute leukemias, malignant lymphomas and solid tumors (Table 1). However, several of these aberrations are more important than others because of their high frequency or because of their prognostic value. For instance, t(14;18) occurs frequently in NHL, whereas t(12;21) is frequently found in childhood precursor-B-ALL. On the other hand, translocations involving the MLL gene in the 11q23 region represent a poor prognostic factor and the presence of 11q23 (MLL gene) aberrations is already in use as an important factor for stratification of treatment in acute leukemias. Also t(9;22) in ALL has a poor prognosis and is used for treatment stratification.

The MLL (for myeloid-lymphoid leukemia or mixed-lineage leukemia) gene in chromosome region 11q23 is involved in several translocations in both ALL and acute myeloid leukemias (AML). In these translocations, the MLL gene, encoding a protein that shows homology to the Drosophila trithorax gene product, is fused to partner genes on different chromosomes. To date, at least ten partner genes have been identified. Some of these translocations, like the t(4;11) (q21;q23), t(11;19) (q23;p13) and t(1;11) (p32;q23), predominantly occur in ALL, whereas others, like t(1;11) (q21;q23), t(2;11) (p21;q23), t(6;11) (q27;q23) and t(9;11) (p22;q23), are more often observed in AML. Other types have been reported in ALL as well as AML. Treatment-induced AML with 11q23 aberrations can arise in patients previously treated with topoisomerase II inhibitors. Rearrangements involving the 11q23 region occur very frequently in infant acute leukemias (around 60–70%), and to a much lesser extent in childhood and adult leukemias (each around 5%). MLL gene rearrangements, especially the t(4; 11), have been shown to be a poor prognostic factor in infant leukemias, resulting in a 3-year overall survival of 5% as compared to 85–90% in cases with germline MLL genes.

The large MLL gene (>100 kb) consists of 21 exons, encoding over 3900 amino acids. Breakpoints in the MLL gene are clustered in an 8.5–9 kb region that encompasses exons 5–11. Because of its relatively small size, this breakpoint region is easily accessible for molecular detection of translocations. By choosing two distinctly labeled FISH probes in the sequences flanking the breakpoint region, any translocation involving the 11q23 region can be detected on the basis of segregation of the two fluorochrome signals, whereas the two fluorochromes colocalize when no rearrangement in the MLL gene has occurred. Furthermore, the use of a third fluorochrome for probes directed against partner genes enables the identification of the precise type of translocation. This two-step approach of FISH analysis guarantees efficient and direct detection of all aberrations involving the 11q23 (MLL gene) region in the first step, whereas in the second step, the type of 11q23 translocation can be determined.

Chromosome aberrations in lymphoid malignancies often involve Ig or TCR genes. Examples include the three types of translocations (t(8;14), t(2;8), and t(8;22)) that are found in Burkitt's lymphomas, in which the MYC gene is coupled to Ig heavy chain (IGH), Ig kappa (IGK), or Ig lambda (IGL) gene segments, respectively. Another common type of translocation in this category is the t(14;18) (q32;q21) that is observed in ~90% of follicular lymphomas, one of the major NHL types. In this translocation, the BCL2 gene is rearranged to regions within the IGH locus within or adjacent to the JH gene segments. The result of this chromosome aberration is the overexpression of the BCL2 protein, which plays a role as survival factor in growth control by inhibiting programmed cell death.

The BCL2 gene consists of only three exons, but these are scattered over a large area. Of these, the last exon encodes a large 3' untranslated region (3' UTR). This 3' UTR is one of the two regions in which many of the t(14;18) breakpoints are clustered and is called "major breakpoint region" (mbr); the other breakpoint region involved in t(14;18) translocations is located 20–30 kb downstream of the BCL2 locus and is called the "minor cluster region" (mcr). A third BCL2 breakpoint area, the vcr (variant cluster region), is located at the 5' side of the BCL2 locus and is, amongst others, involved in variant translocations, i.e., t(2;18) and t(18;22), in which IGK and IGL gene segments are the partner genes.

By choosing a set of FISH probes that is located in the regions upstream of the mbr region and downstream of the mcr region, translocations in these regions can be detected upon segregation of the fluorochrome signals. An additional set of FISH probes is designed for the vcr region, since the distance between the vcr region and the other two breakpoint clusters is far too large (~400 kb) to use the same probes. As a second step in all these approaches, FISH probes in the IGH, IGK, and IGL genes are used for identification of the exact type of translocation.

Several types of nucleic acid probes can be employed in FISH technology as provided by the invention for detection of chromosome aberrations. Each of these probe types has its own characteristic features and advantages, together constituting a complementary approach, i.e., cosmid-, PAC-, or YAC-derived probes, PCR-based probes, or PNA-based probes.

Clones obtained from cosmid, PAC or YAC libraries constitute large probes that, when labeled with fluorochromes, result in appropriate signals upon hybridization (Gingrich et al., 1996). However, conventionally as the precise position of these probes is unknown, there often is a risk of overlap with the breakpoint cluster region of the involved chromosome aberration if no further selection or modification of these probes is performed. Furthermore, such large probes often contain repetitive sequences, which cause high background staining. Distinct and balanced pairs of probes comprising cosmid, PAC or YAC probes that are designed to react with the flanking regions upstream and downstream of the breakpoint area on one of the involved chromosomes can, therefore, be exactly positioned in fiber FISH experiments by use of Southern blotting using small well-defined inclusion and exclusion probes that are designed around the breakpoint area, avoiding the overlap with the breakpoint cluster. The presence of potential repetitive sequences is excluded via Southern blot analysis of genomic DNA.

Probes that are generated by PCR have the additional advantage that they can be positioned exactly; however, for this approach, sequence information is required at least in the areas for designing the target-specific PCR primers for producing the probes. Once generated, the PCR products are checked for the presence of repetitive or cross-hybridizing sequences that hamper specific detection of the flanking regions upstream and downstream of the involved breakpoint cluster. PNA-based probes for FISH technology comprise multiple (e.g., 50–150) distinct PNA oligonucleotides, each of which shows a typical size of 5–40 nucleotides, more typically 10–25 nucleotides, and which together produce an appropriate signal for detection of chromosome aberrations using FISH technology. PNA probes having a neutral peptide backbone to which the four deoxynucleotides are coupled are stable nucleic acid fragments that hybridize to complementary nucleic acid sequences with high affinity (Egholm et al., 1993; Corey, 1997). Due to the fact that mismatches strongly influence PNA hybridization, sequence specificity of PNA recognition can be easily achieved, thereby rendering PNA probes as highly selective probes to be used in FISH technology. PNA probes have now been used in a variety of applications, including in situ hybridization to highly repetitive centromeric or telomeric sequences (Corey, 1997). Thus far, only a single PNA oligonucleotide directed against repeated sequences was sufficient for appropriate signal intensities. The design of a balanced pair of nucleic acid probes comprising multiple (e.g., 50–150) distinct PNA oligonucleotides directed against target sequences in the flanking regions of a breakpoint cluster provides detection of chromosome aberrations as well as with other nucleic acid probes.

Applicability of the Various Types of Probes

Each of the previously herein-mentioned types of FISH probes has its specific applicability, but together they constitute complementary and partly overlapping strategies.

The MLL gene in chromosome region 11q23 is an example of a detectable region that is involved in several translocations in both ALL and AML (Table 1), providing a perfect example of a chromosome aberration for which PCR-based or PNA-based FISH probes can preferably be designed. Because the breakpoint area in the MLL gene is so tightly clustered with ample exons available in the flanking regions upstream and downstream of the breakpoint cluster, sequence-based design and production of distinct and balanced pairs of PCR-based and/or PNA-based FISH probes is very useful in this chromosome region. Design of precisely positioned cosmid or PAC clones could be useful as an alternative or additional strategy.

For example, the BCL2 gene area is involved in several chromosome aberrations in malignant lymphomas (Table 1) and contains several breakpoint areas that are located outside the coding sequence at the 5' and 3' sides of the BCL2 locus and lie far apart. The BCL2 locus, therefore, exemplifies a gene involved in chromosome aberrations for which distinct and balanced pairs of FISH probes are more difficult to generate via PCR and/or via pooling of PNA oligonucleotides, as less sequence information is available. In such chromosome aberrations, distinct and balanced pairs of cosmid-, PAC-, and/or YAC-derived FISH probes can be employed after careful selection and modification of the exact position.

Although the invention has been explained with reference to certain specific details and illustrative examples, the scope of the invention is to be determined by the appended claims.

REFERENCES

1. Gingrich J. C., Boehrer D; Garnes J. A., Johnson W., Wong B., Bermann A., Eveleth G. G., Longlois R. G., Carrano A. V., Construction and characterization of human chromosome 2-specific cosmid, fosmid, and PAC clone libraries. *Genomics* 1996:32:65–74.
2. Egholm M., Buchard O., Christensen L., Behrens C., Freier S. M., Driver S. A., Berg R. H., Kim S. K., Noreden B., Nielsen P. E., PNA hybridizes to complementary oligonucleotides obeying the Watson-Crick hydrogen-bonding rules. *Nature* 1993:365:566–568.
3. Corey D. R., Peptide nucleic acids: expanding the scope of nucleic acid recognition. *Tibtech* 1997;15:244–229.
4. Wiegant J., Kalle W., Mullenders L., Brookes S., Hoovers J. M. N., Dauwerse J. G., Van Ommen G. J. B., Raap A. K., High-resolution in situ hybridization using DNA halo preparations. *Hum. Mol. Genet.* 1992:5:17–21.
5. Young B. D., and Saha V., Chromosome abnormalities in leukaemia: the 11q23 paradigm. *Cancers Surveys* 1996; 28:225–245
6. Nilson I., Löchner K., Siegel G., Griel J., Beck J. D., Fey G. H., Marschalek R., Exon/ingron structure of the human ALL-1 (MLL) gene involved in translocations to chromosomal region 11q23 and acute leukaemias. *Br. J. Haematol.* 1996;93:966–972.
7. Taki T., Ida K., Bessho F., Hanada R., Kikuchi A., Yamamoto K., Sako M., Tsuchida M., Seto M., Ueda R., Hayashi Y., Frequency and clinical significance of the MLL gene rearrangements in infant acute leukemia. *Leukemia* 1996;10:1303–1307.
8. Gascoyne R. D., Adomat S. A., Krajewski S., Kajewska M., Horsman A., Tolcher A. W., O'Reilly S. E., Hoskins, Coldman A. J., Reed J. C., Connors J. M., Prognostic significance of Bcl-2 protein expression and Bc12-gene rearrangement in diffuse aggressive Non-Hodgkin's lymphoma. *Blood* 1997;90:244–251.
9. Seto M., Jaeger U., Hockett R. D., Graninger W., Benett S., Goldman P., Korsmeyer S. J., Alternative promoters and exons, somatic mutation and deregulation of the BCL2-lg fusion gene in lymphoma. *EMBO J.* 1988;7: 123–131.
10. Seite P., Leroux D., Hillion J., Monteil M., Berger R., Mathieu-Mahul D., Larsen C. J. Molecular analysis of a variant 18;22 translocation in a case of lymphocytic lymphoma. *Genes Chrom Cancer* 1993;6:39–44.
11. Tashiro S., Takechi M., Asou H., Takauchi K., Kyo T., Dohy H., Kikuchi M., Kamada N., Tsjujimoto Y., Cytogenetic 2;18 and 18;22 translocation in chronic lymphocytic leukemia with juxtaposition of bcl-2 and immunoglobulin light chain genes. *Oncogene* 1992;7:573–577.
12. Hibshoosh H., Lattes R., Immunohistochemical and molecular genetic approaches to soft tissue tumor diagnosis: a primer. *Semin. Oncol.* 1997;24:515–525.
13. Zoubek A., Dockhorn-Dworniczak B., Delattere O., Christiansen H., Niggli F., Gatterer-Menz I., Smith T. L., Jürgens H., Gadner H., Kovar H., Does expression of different EWS chimeric transcripts define clinically distinct risk groups of Ewing tumor patients? *J. Clin. Oncology* 1996;14:1245–1251.

TABLE 1

Examples of chromosome aberrations in malignancies that are detectable with a distinct and balanced pair of nucleic acid probes of the invention.

| Translocation | Involved genes | Primary target gene for FISH probe design | Occurrence per disease category |
|---|---|---|---|
| Acute leukemias | | | |
| t(4;11) (q21;Q23) | MLL-AF4 | | 70% of infant ALL |
| t(11;19) (q23;p13) | MLL-ENL | | 5–7% of ALL |
| t(6;11) (q27;q23) | MLL-AF6 | | 5–6% of AML |
| t(9;11) (p22;q23) | MLL-AF9 | MLL gene | |

TABLE 1-continued

Examples of chromosome aberrations in malignancies that are detectable with a distinct and balanced pair of nucleic acid probes of the invention.

| Translocation | Involved genes | Primary target gene for FISH probe design | Occurrence per disease category |
|---|---|---|---|
| Malignant lymphomas | | | |
| t(14;18) (q23;q21) | BCL2-IGH | | 90% of follicular NHL |
| t(2;18) (p12;q21) | IGK-BCL2 | BCL2 gene | 25% of immunoblastic NHL |
| t(18;22) (q21;q11) | IGL-BCL2 | | 25% of diffuse large cell centroblastic NHL |
| | | | 5–10% of B-CLL |
| Solid tumors | | | |
| t(11;22) (q24;q12) | EWS-FLI1 | | |
| t(21;22) (q22;q12) | EWS-ERG | | |
| t(7;22) (p22;q12) | EWS-ETV1 | EWS gene | >95% of Ewing sarcoma |

What is claimed is:

1. A pair of nucleic acid probes for the detection of at least one chromosomal aberration in interphase nuclei by in situ hybridization,
wherein each of the nucleic acid probes is larger than 25 kb,
wherein each of the nucleic acid probes is labeled directly or indirectly with at least one different reporter molecule,
wherein the at least one different reporter molecule is chosen from fluorochromes,
wherein each of the nucleic acid probes hybridizes to a sequence such that the pair of nucleic acid probes would flank a potential breakpoint of a chromosome upon hybridization to the chromosome,
and wherein the nucleic acid probes hybridize at a genomic distance resulting in colocalization of the reporter molecule signals if no chromosome aberration is present.

2. A pair of nucleic acid probes according to claim 1, wherein the pair of nucleic acid probes are labeled with the at least one reporter molecule resulting in signals of comparable intensity between the pair of nucleic acid probes.

3. A pair of nucleic acid probes according to claim 1, wherein the combination of relative size of each of the nucleic acid probes, intensity of the at least one reporter molecule labeling each of the nucleic acid probes, and genomic distance between each of the nucleic acid probes following hybridization to the chromosome, results in signals from the nucleic acid probes of comparable intensity.

4. A pair of nucleic acid probes according to claim 1, wherein each of the nucleic acid probes is made up of multiple oligonucleotides.

5. A pair of nucleic acid probes according to claim 1, wherein there is no overlap of the pair of nucleic acid probes with the breakpoint cluster region of the chromosome.

6. A pair of nucleic acid probes according to claim 1, wherein each of the nucleic acid probes does not contain major repetitive sequences.

7. A pair of nucleic acid probes according to claim 1, wherein the pair of nucleic acid probes hybridizes to a single corresponding nucleic acid molecule.

8. A pair of nucleic acid probes according to claim 7, wherein the corresponding nucleic acid molecule is at least a fragment of a chromosome.

9. A pair of nucleic acid probes according to claim 1, wherein the pair of the nucleic acid probes hybridize at a genomic distance of no more than 100 kb between each of the nucleic acid probes.

10. A diagnostic kit comprising at least a pair of nucleic acid probes for the detection of at least one chromosomal aberration in interphase nuclei by in situ hybridization,
wherein each of the nucleic acid probes is larger than 25 kb,
wherein each of the nucleic acid probes is labeled directly or indirectly with at least one different reporter molecule,
wherein the at least one different reporter molecule is chosen from fluorochromes,
wherein each of the nucleic acid probes hybridizes to a sequence such that the pair of nucleic acid probes would flank a potential breakpoint of a chromosome upon hybridization to the chromosome,
and wherein the nucleic acid probes hybridize at a genomic distance resulting in colocalization of the reporter molecule signals if no chromosome aberration is present.

11. A diagnostic kit according to claim 10 further comprising at least one additional nucleic acid probe.

* * * * *